US00PP12443P2

(12) United States Plant Patent
Cummins et al.

(10) Patent No.: US PP12,443 P2
(45) Date of Patent: Mar. 12, 2002

(54) APPLE ROOTSTOCK NAMED 'GENEVA 16'

(75) Inventors: James N. Cummins; Herbert S. Aldwinckle, both of Geneva, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/372,808

(22) Filed: Aug. 12, 1999

(51) Int. Cl.[7] ..... A01H 5/00
(52) U.S. Cl. ..... Plt./174
(58) Field of Search ..... Plt./174

*Primary Examiner*—Bruce R. Campell
*Assistant Examiner*—Susan B. McCormick

(57) ABSTRACT

A new and distinct apple rootstock, 'Geneva 16' is a dwarfing rootstock that is resistant to fire blight.

4 Drawing Sheets

TECHNICAL FIELD

This invention is directed to an apple rootstock.

BACKGROUND OF THE INVENTION

'Malling 9' rootstock is susceptible to crown and root rots and extremely susceptible to fire blight.

The goal herein was a dwarfing apple rootstock that is resistant to fire blight.

SUMMARY OF THE INVENTION

The present invention relates to a new and distinct cultivar of apple tree rootstock, 'Geneva 16', which we discovered in a test planting belonging to New York State Agricultural Experiment Station, Cornell University, Geneva, Ontario County, New York. This discovery is a product of the apple rootstock breeding program of the New York State Agricultural Experiment Station ('Station').

Origin: In March, 1981, pollen was collected from a *Malus floribunda* cv. 821 apple tree and used to pollinate emasculated flowers of a *Malus×domestica* cv. Ottawa 3 apple tree growing in Station greenhouse No. 13. The seeds were harvested from fruit produced from this cross and were stratified in November, 1981. After stratification, 560 germinating seeds were planted in a Station greenhouse in January, 1982. When the emerging seedlings were about 2.5 cm tall, they were inoculated with 15 isolates of the fungi *Phytophthora cactorum* and *Phytophthora megasperma*, which are causal agents of certain crown and root rots. The flats were flooded to mid-hypocotyl level of the seedlings, and kept at about 23° C. for seven days; 127 seedling survived this treatment. The surviving seedlings, when 10 to 15 cm tall, were inoculated in their shoot tips with about $10^6$ cells of isolate Ea 273 of the bacterium *Erwinia amylovora*, the causal agent of the fire blight disease, using a 26-gauge hypodermic syringe. Three subsequent inoculations with *E. amylovora* isolate Ea 273 were made in summer and autumn, 1982. All but 14 of the seedlings were discarded for susceptibility to fire blight or were killed by fire blight. The seedling designated 6103FL-016, later tested as CG.16 and now named 'Geneva 16', was very resistant. Lesions that developed from the greenhouse inoculations and later in the field were less than 1 cm long, with some <1 mm long. Later, lesions 2 to 2.5 cm long developed when CG.16 shoots were inoculated with E4001A, a very virulent strain of the bacteria. The survivors were inoculated repeatedly with woolly apple aphids (*Eriosoma lanigerum*); very susceptible individuals were discarded. Seedings with very small leaves and those displaying either root initials or spines were also discarded.

The plant now designated 'Geneva16' was moderately susceptible to woolly aphids when inoculated with the local wild type. Leaves and fruit of 'Geneva16' are immune to apple scab (*Venturia inaequalis*) (CG.16's pollen parent, *Malus floribunda* cv. 821, carries the Vigene for immunity to scab). Leaves and shoots are moderately susceptible to powdery mildew (*Podosphaera leucotricha*).

We planted the 14 *Erwinia amylovora*-resistant seedlings as trench layers on the Station's Loomis Farm in April, 1983. Rooted liners were harvested in late fall 1984 and were planted in the Station nursery in the spring, 1985. Maiden trees of the cultivars 'Topred Delicious', 'Pagenelli Delicious', 'Summerland McIntosh' and 'Mutsu' were produced by grafting onto 'Geneva 16' liners. These trees were subsequently planted in trial orchards at the Station and at the United States Department of Agriculture Appalachian Fruit Research Station, Kearneysville, W. Va.; Washington State University Tree Fruit Research and Extension Center, Wanatchee, Wash; Littletree Orchards, Newfield, N.Y.; and Brown Orchards, Ithaca, NY.

In these test plantings, trees on 'Geneva 16' were similar in size to those on 'Malling 9' EMLA rootstock, based on comparison with the check trees in the same testing plantings. None of the trees on other clones from the 'Ottawa 3'×*Malus floribunda* family were dwarfed. Trees on 'Geneva 16' began flowering early, usually the second year in the orchard; this wes especially noteworthy for 'Mutsu' cultivar, which in New York normally begins fruiting in the third or fourth year when grafted on the precocity-inducing rootstock 'Malling 9'. All of the culivars that have been tested on 'Geneva 16' have demonstrated high production efficiency, similar to that experienced with the very efficient 'Malling 9' rootstock.

Compatibility: We have observed no symptoms of incompatibility with 26 trees of the four fruiting cultivars mentioned above. Besides these, we have grafted 'Jonagold' on 'Geneva 16'; in the nursery we have observed no symptoms of incompatibility. All scionwood used was free from known harmful viruses. Virus sensitivities of 'Geneva 16' are not known.

Propagation: We have propagated 'Geneva 16' asexually by budding and grafting onto seedling and clonal rootstocks; by root cuttings; by hardwood cuttings; by greenwood cuttings; and by conventional layering. These asexual propagules have remained true-to-type with these methods of asexual propagation.

We have also propagated 'Geneva 16' readily in vitro. 'Geneva 16' appears not to be prone to epigenetic changes induced by the growth regulator environment in the tissue culture medium. In layerbeds established with micropropagated 'Geneva 16' plants, rooting has been superior to that observed in conventional layerbeds.

We have also used 'Geneva 16' as a pollen parent in our breeding program; since 'Geneva 16' is highly heterozygous, its seedlings are much different from both parents and from each other, but the excellent resistances to Phytophthora and to *Erwinis amylovora* transmitted to a substantial percentage of progeny.

The photographs of FIGS. 1, 2, 3 and 4 were taken with a digital camera and are of digital camera quality.

DETAILED DESCRIPTION

Descriptions: Following is a detailed description of our new rootstock culivar, 'Geneva 16'. The numerical color specifications employed are those of The Royal Horticultural Society Colour Chart (1976). Botanical descriptions follow Manual of Cultivated Plants (Bailey, 1949).

Tree habit: The unbudded tree of 'Geneva 16' is a small shrub, typically standing about 1 m tall×about 1.5 m wide when 10 years old. There is no single dominant trunk, but rather 3 to 6 branches arising near the base of the tree. Branch size will vary with the age of a tree but typically will be 2 cm in diameter at two years. The branches will grow to about 1–1.5 meters long in 10 years and typically have a crotch angle of about 50 degrees. Branch color is brown 200B. Branch texture is smooth. The unbudded tree is a dwarf, comparable to a 'Malling 9' apple tree of similar age but differing from 'Malling 9' in having no suckers. Growth rate is moderately slow, with early cassation of growth typically occurring about the same time as 'Malling 9'. Spring budbreak is midseason. Autumn leaf fall is moderately early, about the same as 'Malling 9'. Suckers are rare; a total of 5 suckers have been observed on the 26 trees tested in the orchard. As an unbudded plant, 'Geneva 16' is very precocious; we have even occasionally observed flowers on two-year old stems in the layerbed.

Figure 1:
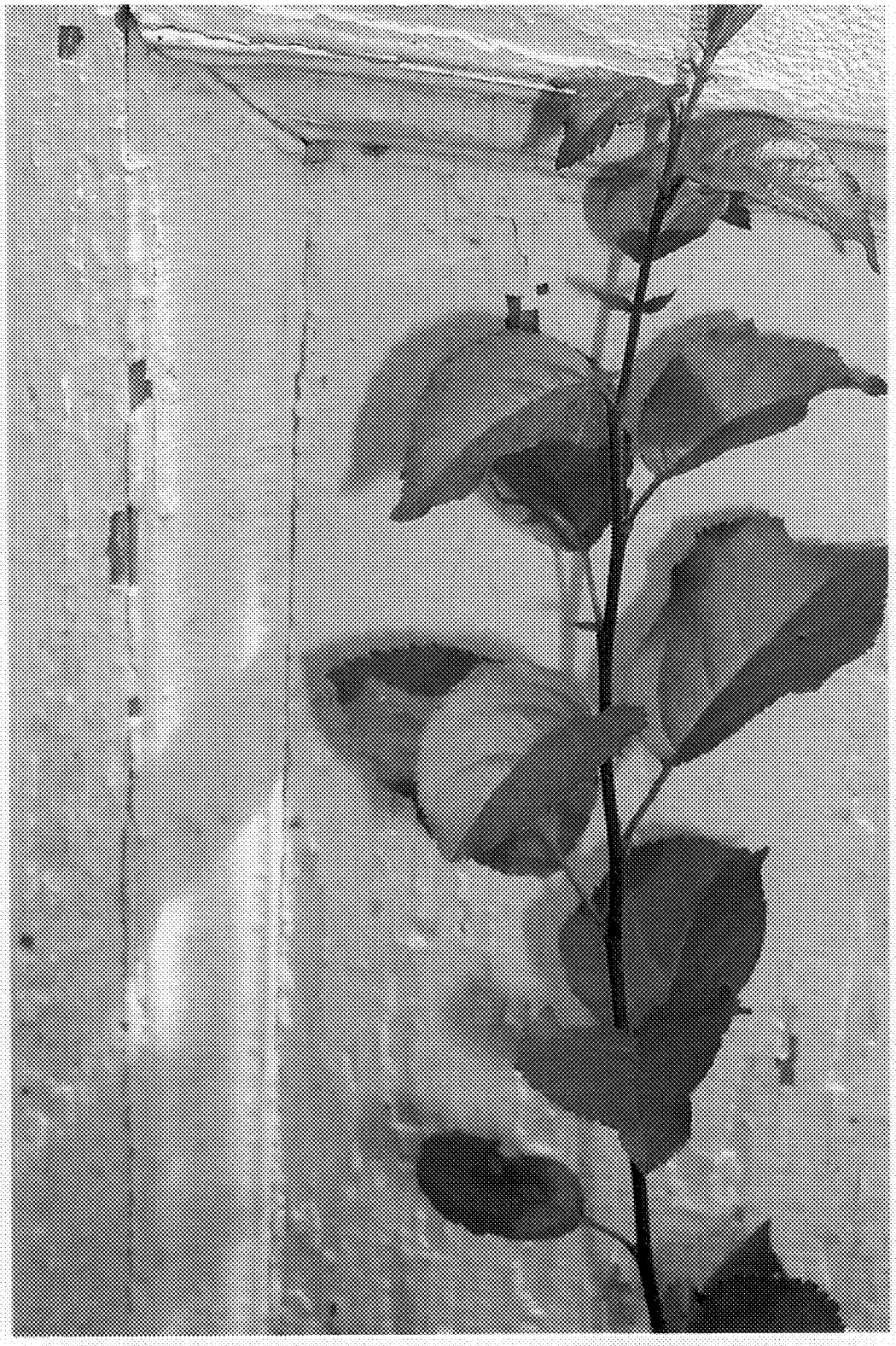
FIG. 1 is a print from an e-mail communication showing a rootsucker growing in a pot in a greenhouse simulating fall growth.

Dormant Shoots: A stoolbed is present in the field in the fall. A rootsucker growing in a pot in a greenhouse simulating fall growth is shown in FIG. 1. A plurality of such rootsuckers make up a stoolbed. In the stoolbed and nursery row, dormmant matured shoots of current season are brown 200B where exposed to full sunlight, grading to greyed-orange 166A with diminished light exposure. Two-year-old shoots are grey-brown 199A. Pubescence is very light. Shoots are of below average vigor, usually about 50 to 70 cm in the stoolbed, similar to 'Malling 9' and 'Ottawa 3'. Shoots are 5–10 mm in diameter. Midshoot internodes are average, ranging from 23 to 28 mm. Axillary buds are obtuse, sessile, usually somewhat appressed. Axillary buds are about 5 mm long by 3 mm wide. Axillary buds may be vegetative only, mixed vegetative and generative, or generative only. Bud scales are average size, greyed-orange 177A to 177C with moderate greyed-white 156D pubescence at the bud tip. Bud scales are about 1 mm long and about 0.5 mm wide and are conical. Lenticels are round, small in size, mostly 0.2 to 0.3 mm diameter, very slightly raised, greyed-orange 165C in midshoot section. We have observed no burrknots on the 26 trees in test orchards and no root germs on young shoots in the layerbed. No sphaeroblasts have been observed. Wood is not brittle; breaking strength (as determined by breaking sticks by hand and rating compared to other sticks) of 'Geneva 16' is similar to that of 'Malling 26'. A very few spines have been observed on young shoots from a layerbed established with micropropagated plants.

Figure 2:
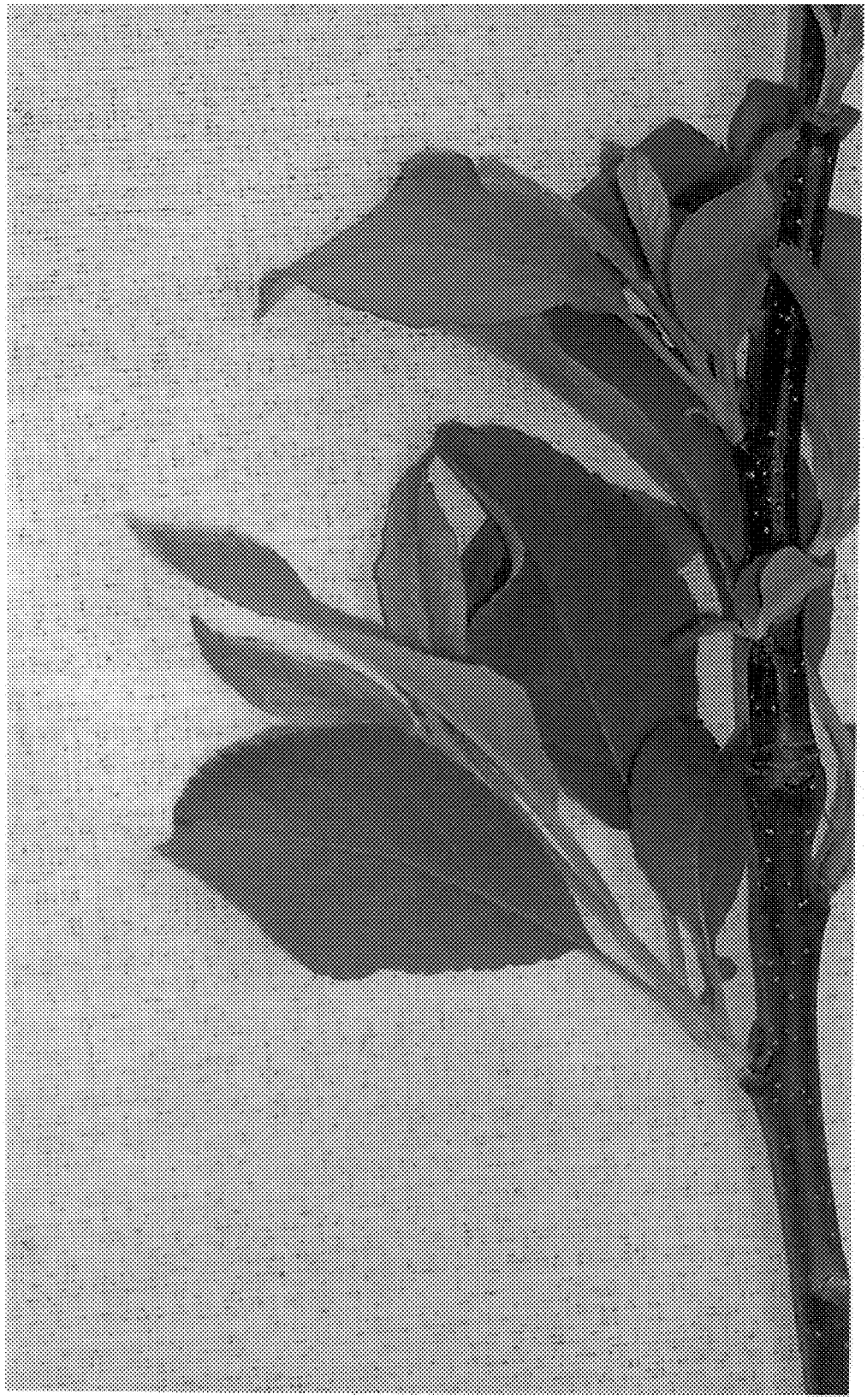
FIG. 2 is a print from an e-mail communication of a branch from a 'Geneva 16' tree during spring bloom showing the leaves.
Figure 3:
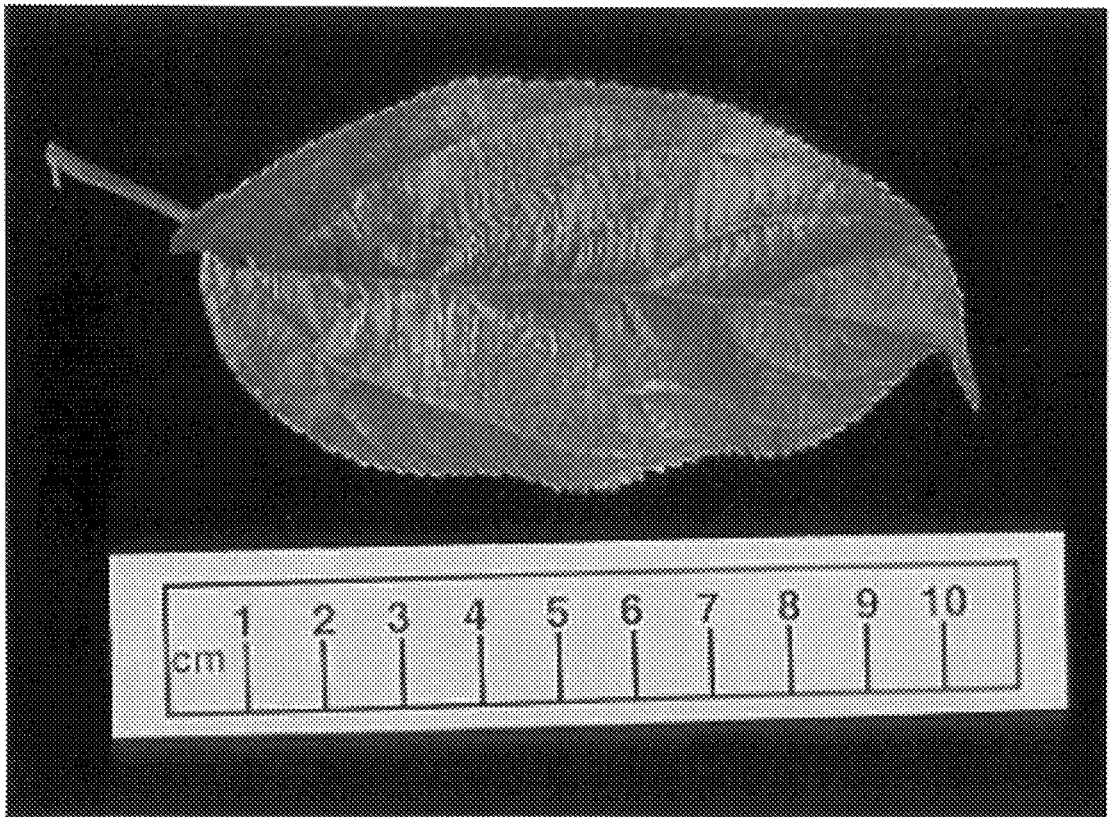
FIG. 3 is a print from a web site showing a leaf of a 'Geneva 16' liner during late summer and indicating dimensions thereof.

Leaves: Simple, oblong-ovate; lamina somewhat wavy; tip acuminate; margin acutely serrate; about 4 serrations per cm; base obtuse, usually symmetrical or nearly so. Stipules are absent or small, up to 1×10 mm. Stipules are brown-orange 172B. Laminae average 99.5 mm long× 55.0 mm wide. Average petiole length is 21.4 mm. Petioles are 2 mm in diameter and green 141C. Adaxial lamina surface is green 137A; abaxial surface is yellow-green 148B; upper surface is smooth and nearly glabrous; lower side has soft short pubescence. Leaves on the same plant are different in color. The colors described are exemplary of one leaf and not of the leaves of the entire plant. Leaf poise typically 15° to 25° from shoot. A branch from a 'Geneva 16' tree during spring bloom displaying the leaves thereon is shown in FIG. 2. The leaf arrangement is alternate. The leaves are recurved. A single leaf of a 'Geneva 16' liner during late summer is shown in FIG. 3. The venation pattern is netted.

Figure 4:
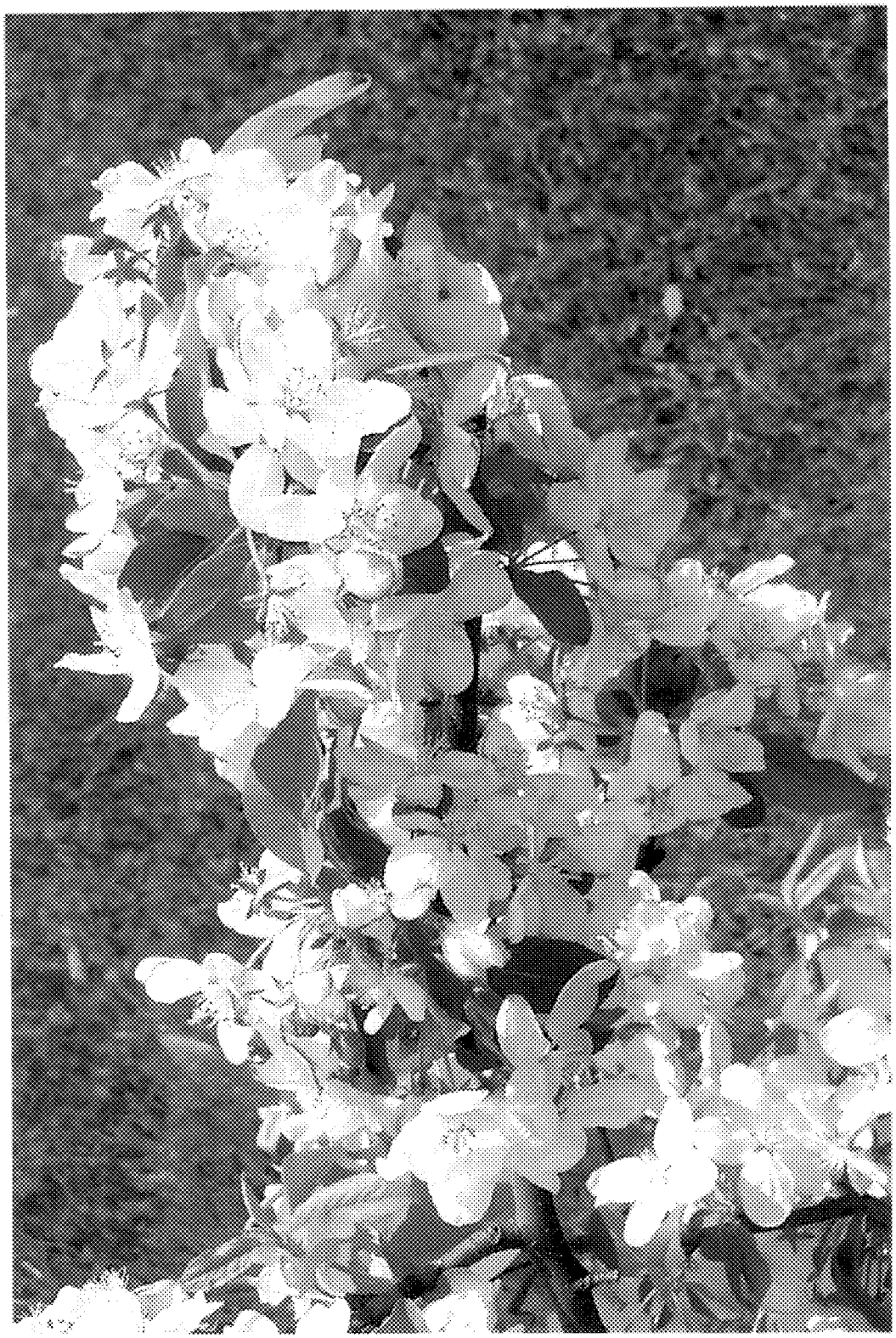
FIG. 4 is a print from an e-mail communication of springtime bloom of a 'Geneva 16' tree.

Flowers and fruit: Flowering is regular and abundant, even in the year following a heavy crop. Flowers are borne on spurs, on shoot terminals, and from lateral buds on growth of the previous season. Lateral buds are obtuse, sessile and usually somewhat appressed and 4 mm long by 3 mm wide. Buds on spurs and terminals are mixed, typically producing a truss of 6 or 7 flowers and 2 bourse shoots. Buds near the base of a shoot of the previous season usually produce 3 to 5 flowers and a single short shoot; midshoot buds may have 2 to 4 flowers; and more distal buds are usually vegetative. Petals are 25 mm in length, 18 mm in width, with ovoid shape, pointed apex, straight base, smooth margin and smooth texture, and the color of the petals closed is pink 54A and of the petals open is white 155D. The flower diameter is 40 mm. Springtime bloom of a 'Geneva 16' tree is shown in FIG. 4. The flowers have no characteristic fragrance.

The pistils are 6 mm in length and yellow-white 145B. Stamen is 4 mm in length and white 155D. Anther color is yellow-brown 167D.

Fruit matures late, about 2 weeks after 'Delicious', and senesces rapidly while still attached to the shoot. Fruits are globose, occasionally globose-conical. Average fruit diameter is 21.6 mm, length 18.5 mm, peduncle 22.3 mm. At maturity, skin color is a bright, glowing red (RHS=44A to 44B, sometimes grading to 43A to 43B); ground color is yellow (RHS=11D) but when fruit is mature this is completely masked by red overcolor. We have seen no russet. Flesh is firm, very fine-grained, yellow (RHS=8D) when freshly cut but browning very quickly when exposed to air. Flavor is moderately astringent, acidic, with little aroma. Seeds are 4–6 mm long and 3 mm wide and have the shape of elongated spheres. Seeds are greyed orange (RHS=177B) in 5 locules. Calyxes are adherent until a few days before fruit maturity, at which time 50 to 75% abscise.

Distinguishing From 'Malling 9' and 'Ottawa 3' Rootsocks: 'Geneva 16 ' may be distinguished from 'Malling 9' in that the latter has numerous spines; occasional burrknots; numerous suckers; greenish-brown shoots; is very susceptible to fire blight; and has yellow fruits that are much larger than those of 'Geneva 16' and ripen about 7 weeks earlier. 'Geneva 16' may be distinguished from 'Ottawa 3' in that the latter has much larger leaves, especially wider; is very susceptible to fire blight; and fruits are yellow, are somewhat larger than those 'Geneva 16', and ripen about 5 weeks earlier.

Usefulness: 'Geneva 16' is a dwarfing apple rootstock that will directly challenge the 'Malling 9' rootstock, which is more susceptible to crown and root rots and extremely susceptible to fire blight. 'Geneva 16' survived inoculation with two of the most important incitants of crown and root rots; it appears therefore to have tolerance to certain crown and root rots caused by species of the Phytophthora fungus. The fire blight disease is limiting to apple production in many parts of the United States, including California, Washington, the Mid-South and the eastern seaboard states, especially when dwarfing rootstocks in the 'Malling 9' class are desired. 'Geneva 16' is very resistant to fire blight, and 'Geneva 16' will be especially valuable to replace 'Malling 9' in those areas in which fire blight is endemic.

In the orchard, anchorage of grafted trees is much better that of trees on 'Malling 9', which is quite brittle, but because of the precocity induced by 'Geneva 16', permanent support is strongly suggested.

What is claimed is:

1. A new and distinct apple rootstock plant, 'Geneva 16', substantially as described and illustrated herein.

* * * * *